United States Patent [19]

Jovánovics et al.

[11] 4,298,525
[45] Nov. 3, 1981

[54] BIS-INDOLE-ALKALOID

[75] Inventors: Karola Jovánovics; Sándor Görög, both of Budapest, Hungary

[73] Assignee: Richter Gedeon Vegyészeti Gyár RT, Budapest, Hungary

[21] Appl. No.: 61,353

[22] Filed: Jul. 27, 1979

[30] Foreign Application Priority Data

Apr. 23, 1979 [HU] Hungary ............... RI-708

[51] Int. Cl.³ .......................... C07D 519/04
[52] U.S. Cl. .................. 260/244.4; 424/262
[58] Field of Search ............ 260/244.4; 424/195, 424/262

[56] References Cited

U.S. PATENT DOCUMENTS 3,097,137  7/1963  Beer .................................. 167/65
3,205,220  9/1965  Suoboda ......................... 260/244.4
3,354,163  11/1967 Gorman ............................ 260/287
3,370,057  2/1968  Suoboda ............................ 260/236
3,899,493  8/1975  Jovánovics ..................... 260/287 P
4,189,432  2/1980  Jovánovics et al. ............ 260/244.4

Primary Examiner—Donald G. Daus
Assistant Examiner—Diana G. Rivers
Attorney, Agent, or Firm—Karl F. Ross

[57] ABSTRACT

A process for the preparation of diindolealkaloids, especially new compounds corresponding to vinblastine or leurosine, in which the N-methyl group is replaced by an N—$CH_2$—$OC_2H_5$ group having antitumor properties. The starting compounds are subjected to oxidation by chromic acid or an alkali metal dichromate at temperatures from −90° C. to −30° C. but preferably below about −45° C. when the new compounds are to be produced, ethanol being present in this case.

1 Claim, 6 Drawing Figures

Enclosure 1.

RGH-4451-infrared spectrum

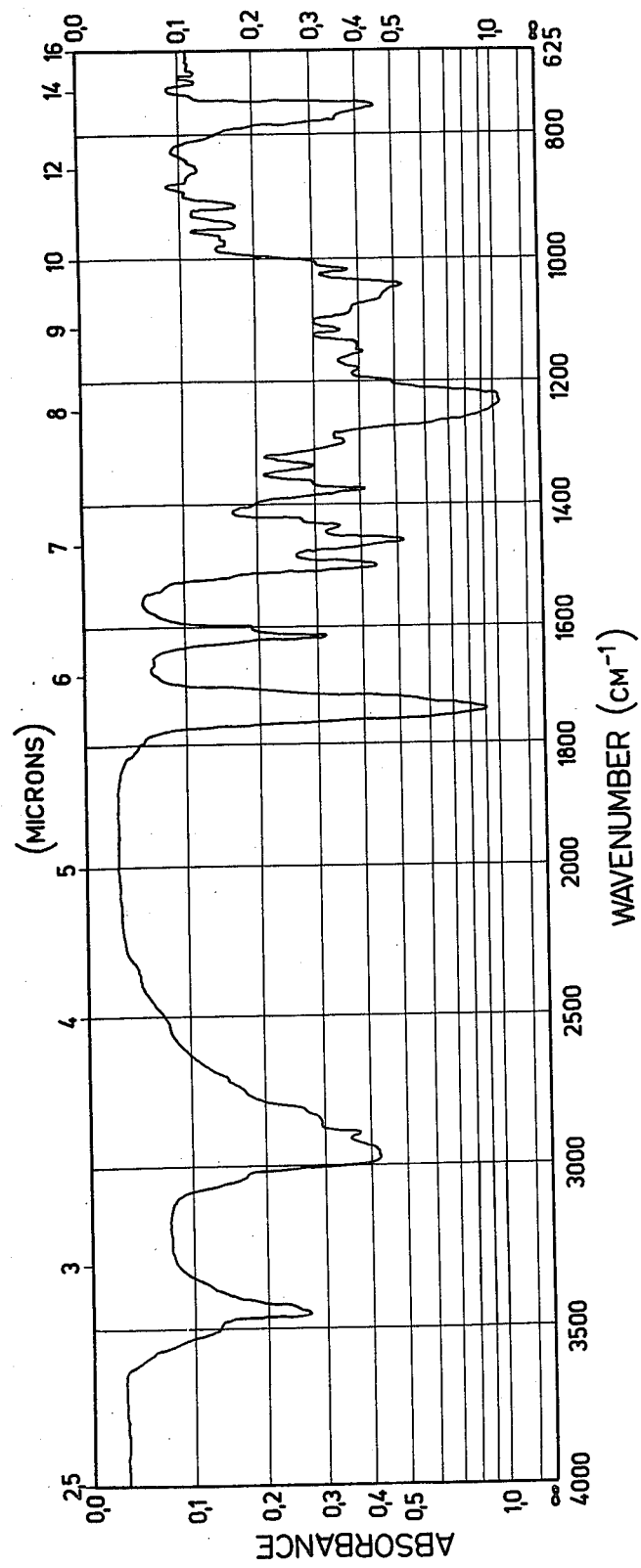
Enclosure 1.
RGH-4451-infrared spectrum

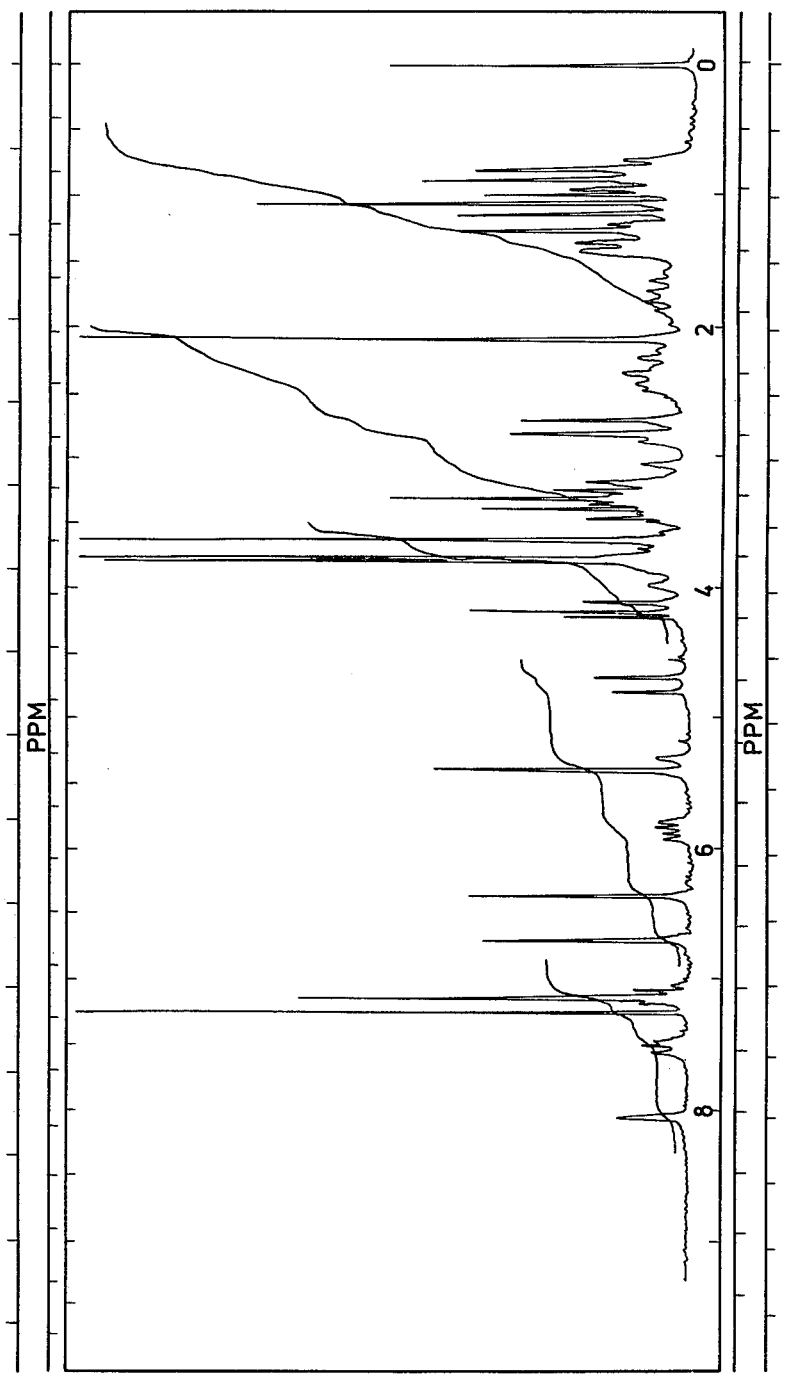
Enclosure 2.
RGH-4451 ¹H-NMR spectrum

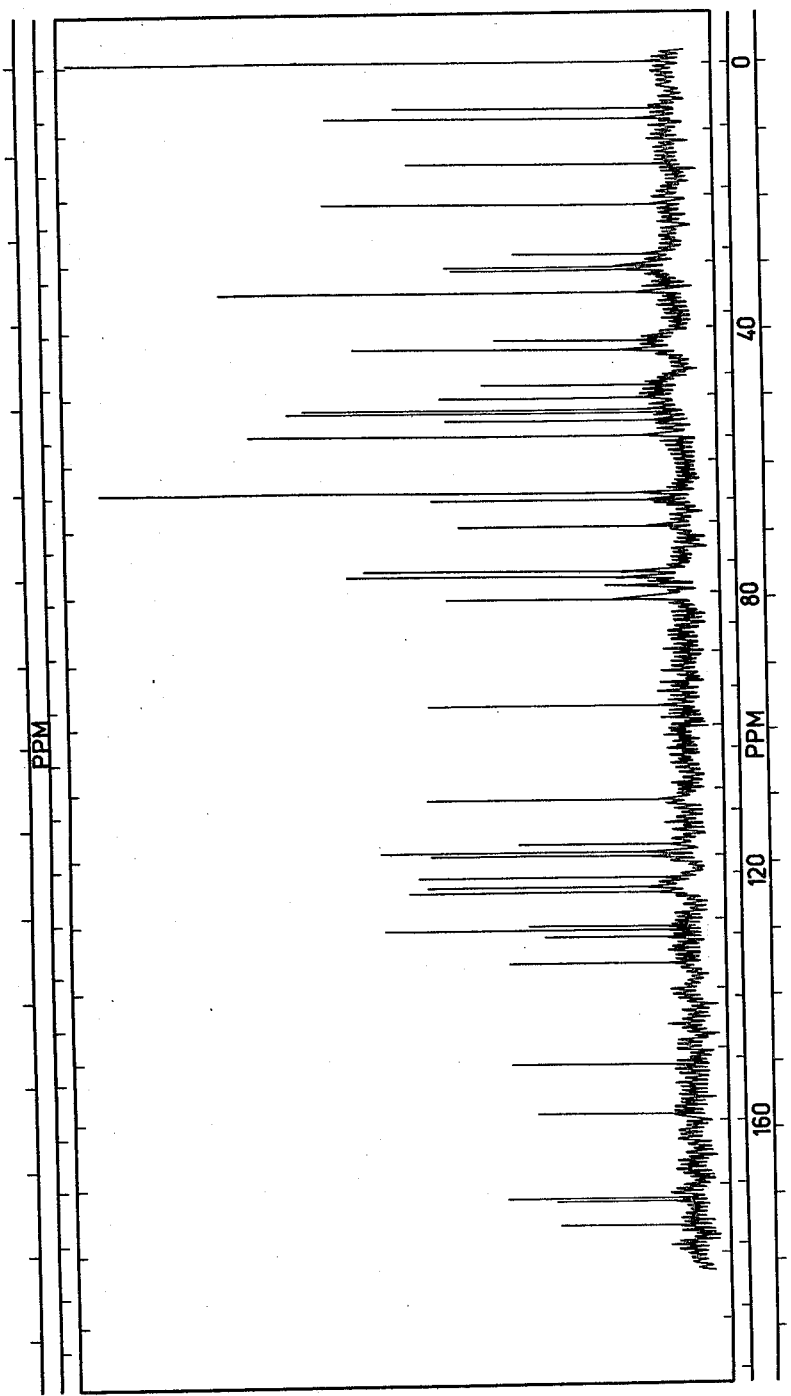

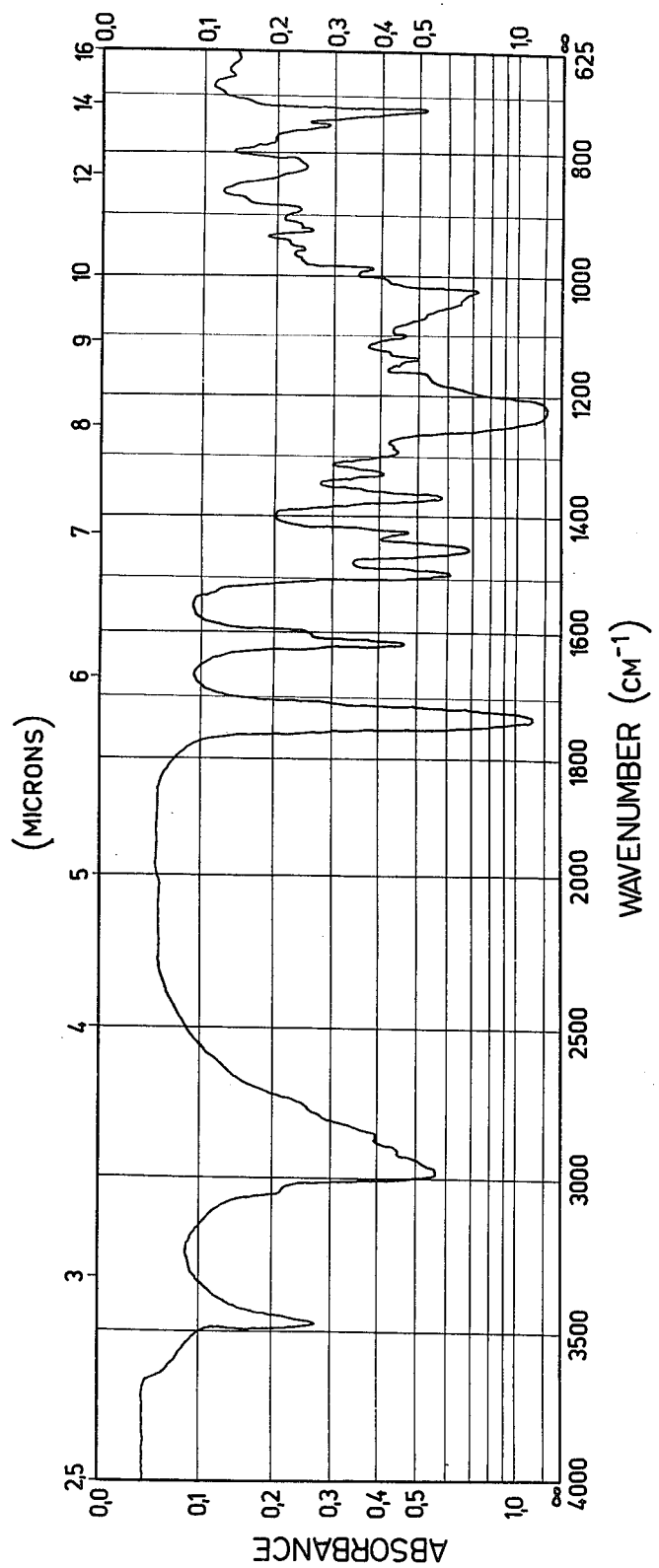
Enclosure 4.
RGH-4478-infrared spectrum

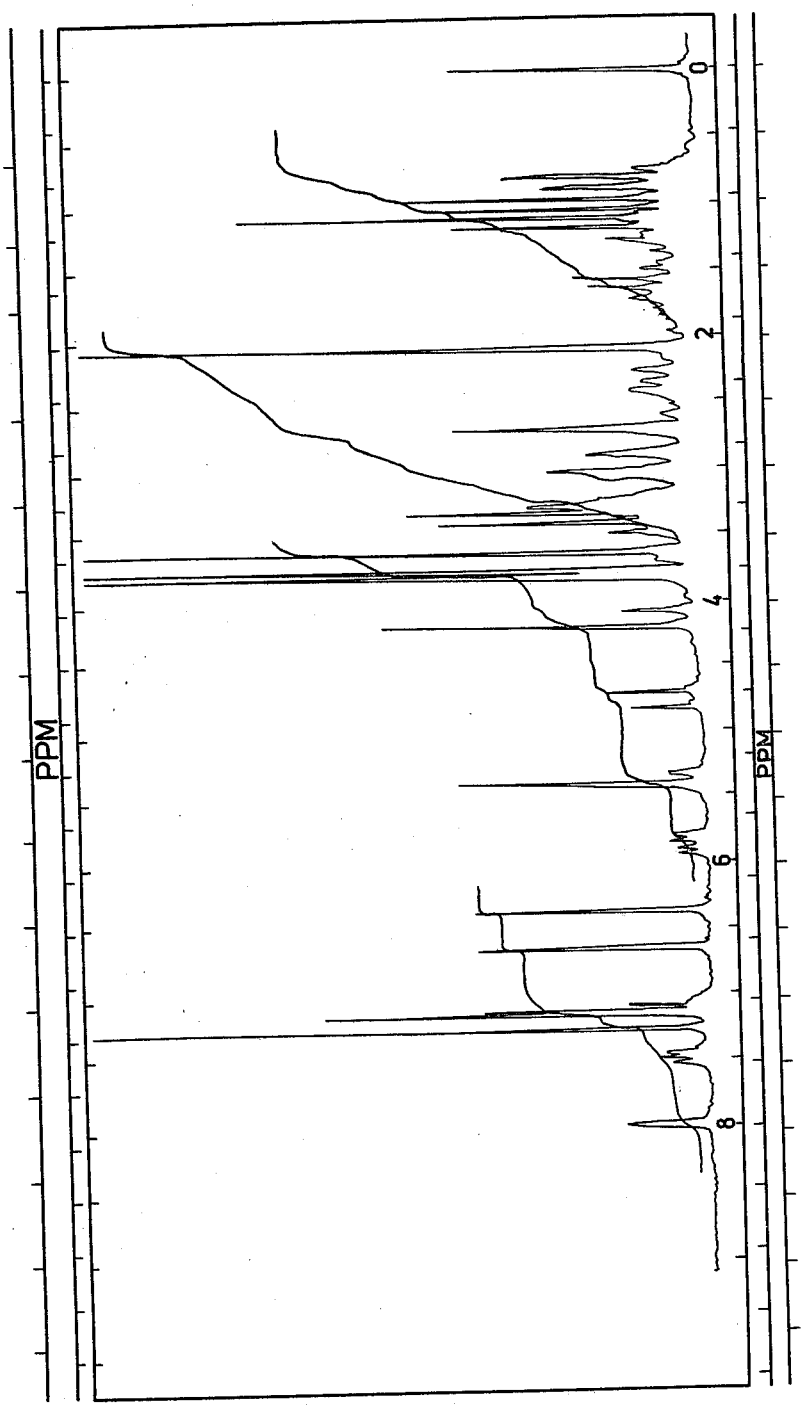
Enclosure 5.
RGH-4478 ¹H-NMR spectrum

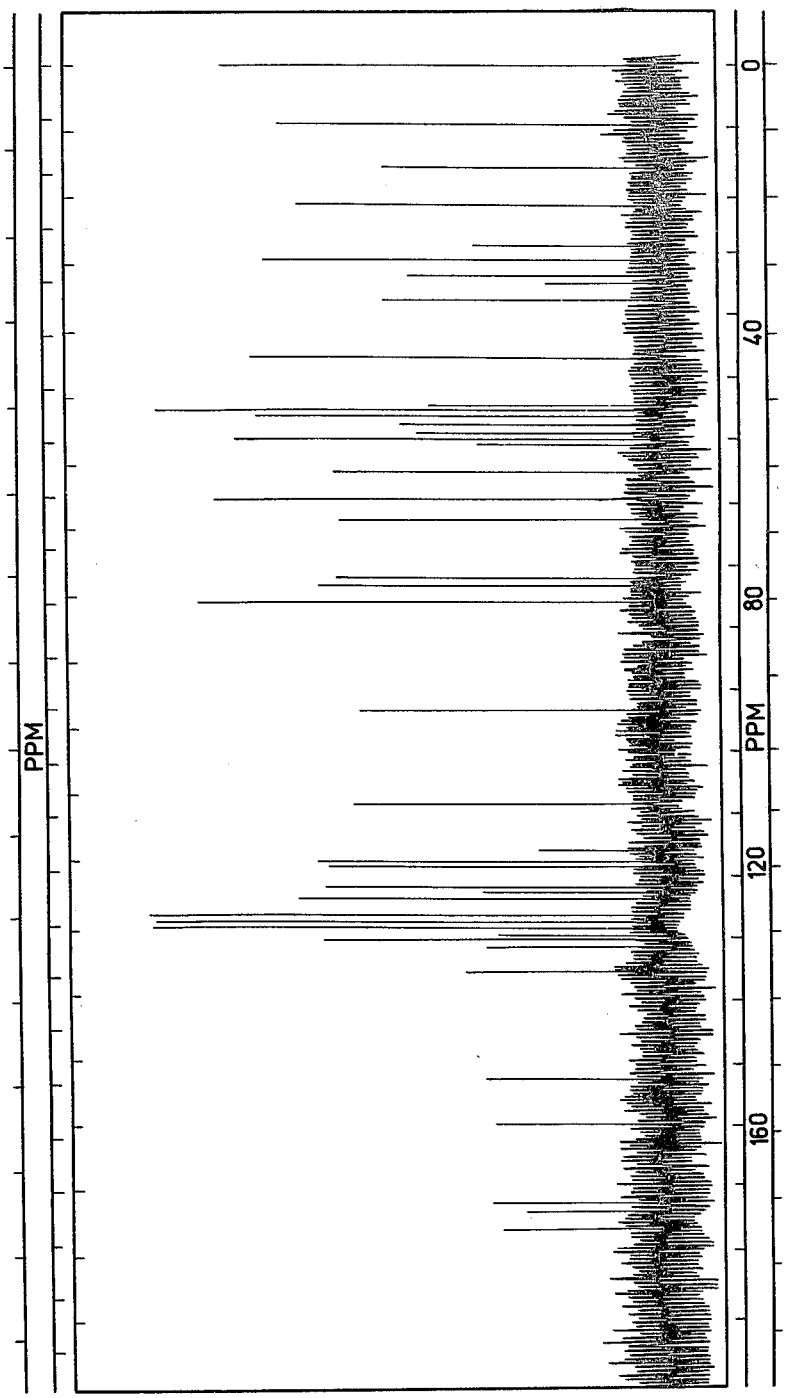
Enclosure 6.
RGH-4478 13C-NMR spectrum

BIS-INDOLE-ALKALOID

The present invention relates to a process for the preparation of bis-indole-alkaloids and acid addition salts thereof, as well as to new bis-indole-alkaloids. More particularly, the invention concerns the oxidation of the N-methyl group of vinblastine, leurosine or the acid addition salts thereof by chromic acid ($CrO_3$) or a salt thereof. Oxidation of vinblastine or an acid addition salt thereof yields the known N-desmethyl-vinblastine and vincristine (also called N-desmethyl-N-formylvinblastine) and also a new compound hereinafter called "RGH-4451". When leurosine or an acid addition salt thereof is oxidized, in addition to the known N-desmethyl-leurosine and N-desmethyl-N-formyl-leurosine another new compound called "RGH-4478" is obtained. The new "RGH"-compounds contain an $N-CH_2-O-C_2H_5$ group in place of the N-methyl group of vinblastine and leurosine, respectively.

The starting compounds used in the process according to the invention are known in the art. Vinblastine and acid addition salts thereof are for example described in the U.S. Pat. No. 3,097,137, while leurosine is the subject of the U.S. Pat. No. 3,370,057. Vinblastine is used as an antitumor agent also in clinical practice. The trade name of the compositions containing vinblastine is Velbe. Also the antitumor activity of leurosine has been proved on animals but it cannot successfully be used in human therapy due to its unreasonably high toxicity on the hematopoietic organs (Rohn, R. et al.: *Cancer Chemother. Reports* 38, 53, 1953).

The preparation of vincristine is for example described in the U.S. Pat. No. 3,205,220, in the Belgian Pat. No. 819,663, in the Hungarian Pat. Nos. 168,433 and 165,599 (corresponding to the U.S. Pat. No. 3,899,493) and in the German Pat. No. 2,614,863; and N-desmethyl-vinblastine can be prepared according to the U.S. Pat. No. 3,354,163, Belgian Pat. No. 819,078 and Hungarian Pat. No. 165,599. N-desmethyl-N-formyl-leurosine and N-desmethyl-leurosine are disclosed in the Hungarian Pat. No. 165,986 (corresponding to the British Pat. No. 1,412,932). N-desmethyl derivatives have no notable antitumor activity. N-formyl derivatives are first of all capable of controlling acute leukemia and various lymphomic deseases; while vincristine is used for the treatment of psoriasis (see U.S. Pat. No. 3,749,784).

Since the use of diindole-alkaloids is accompanied by toxic side effects-for instance the administration of vincristine induces paralytic symptoms due to neurotoxicity-a considerable effort has been made to prepare new derivatives having the same or similar activity without or with less undesired toxic effects. On the other hand, diindole-alkaloids, which cannot be directly utilized for medical purposes are often converted into pharmacologically utilizable alkaloids.

For example according to the process disclosed in the Hungarian Pat. No. 165,986 leurosine is converted into the effective, non-toxic N-desmethyl-N-formyl-leurosine; or according to the Hungarian Pat. No. 165,599 vinblastine is transformed into the more effective N-formyl derivative, i.e. vincristine. According to these processes the starting compound is oxidized with chromium trioxide in a mixture of glacial acetic acid, acetone and acetic anhydride at a temperature between $-90°$ C. and $-30°$ C., whereupon the reaction mixture is neutralized and from the mixture obtained containing N-desmethyl- and N-formyl-leurosine the components are separated, or, if desired, N-desmethyl derivative is converted into the corresponding N-formyl derivative by a suitable formylating agent.

DESCRIPTION OF THE INVENTION

The purpose of this invention is to provide a new oxidation procedure and new oxidative derivatives.

It has surprisingly been found that if the above process acetone is replaced by a water-immiscible organic solvent, in which alkaloids are readily soluble, preferably by a chlorinated hydrocarbon, and a small amount of ethanol, oxidation affords also new compounds. More specifically, oxidation of vinblastine results, in addition to the known compounds, in the formation of a new derivative called "RGH-4451"; and in an analogous way by oxidation of leurosine another new compound indentified as "RGH-4478" is also obtained. The new compounds contain an $N-CH_2-O-C_2H_5$ group in place of the N-methyl group of the starting compounds in the vindoline moiety.

In addition to the new compounds, by the above oxidation the corresponding N-desmethyl- and N-desmethyl-N-formyl derivatives are also obtained. It should be noted that the presence of ethanol is not essential with respect to the formation of the known compounds. The known compounds are always obtained if oxidation is carried out at a temperature of $-30°$ C. to $-90°$ C.

On the other hand the new compounds are only obtained if ethanol is present, and if the temperature of oxidation exceeds $-45°$ C. the new compounds cannot be isolated.

It has further been found that the new "RGH" compounds can be converted into the corresponding known N-desmethyl derivatives by an acid treatment, and the latter compounds can thereafter be converted into the corresponding N-desmethyl-N-formyl derivatives by methods known per se.

The use of a different solvent system also has a technological advantage; due to the two-phase reaction system the oxidation and the subsequent neutralization are less exothermic easy to control and the danger of decomposition of the heat-unstable diindole compounds is considerably decreased. This technological advantage has nothing to do with the presence of ethanol.

The new compounds prepared according to the invention had been subjected to extensive comparative pharmacological tests, and it has been concluded that from a pharmacological point of view RGH-4451 is the most advantageous among the compounds obtained.

The acute toxicity of RGH-4451 was tested on mice. The $LD_{50}$-value of this new compound amounted to 70 mg/kg i.p., which is 17-fold of that of vincristine, about 10-times higher than that of vinblastine and 2.5-times higher than that of N-desmethyl-N-formyl-leurosine.

The lethal dose killed the animals on the 2nd to 5th day. The death was not accompanied by paralytic symptoms, and, in contrast with the results obtained with vincristine, the surviving animals were not crippled even temporarily.

The inhibition of tumor growth was initially studied in a tissue culture. A 20 mg./ml. solution of RGH-4451 in a Fischer medium was prepared and subsequently diluted to the desired concentration. The number of cells in the P 388 cultures was determined 24 and 48 hours after treatment.

In a concentration of $10^{-1}/\mu g./ml.$ the RGH-4451 considerably inhibited the growth of P 388 tumor cells. The inhibition was 43% after 24 hours and 89% after 48 hours. In in vitro tests the compound was 100-times less toxic than vincristine and 4-times less toxic than N-desmethyl-N-formyl-leurosine.

The inhibition of tumor growth was examined also on transplanted rodent tumors.

EFFECT ON P 388 LEUKEMIA TUMORS OF MICE $10^6$ P 388 leukemia cells were transplanted into BDF$_1$ hybrid mice intraperitoneally. Administration of RGH-4451 was started the day following the transplantation. The results obtained are summarized in the following table:

| Dose mg./kg. i.p. | Number of treatments | Frequency | Mean duration of life | | expressed in % of treated/ control |
|---|---|---|---|---|---|
| | | | expressed in days | | |
| | | | Treated | Control | |
| 3.2 | 9 | every day | 22.3 | 12.3 | 181 |
| 5.0 | 9 | every day | 21.5 | 13.2 | 163 |
| 6.4 | 9 | every day | 20.5 | 12.3 | 166 |
| 10 | 5 | every second day | 21.8 | 10.5 | 208 |
| 20 | 6 | every day | 8.5 | 13.2 | 64 |
| 20 | 1 | — | 19.4 | 10.5 | 185 |

From the above results it can be clearly seen that the effect of doses between 1.0 and 6.0 mg./kg. is significant.

EFFECT ON NK/LY ASCITES LYMPHOMA

Tests were carried out analogously with the Ehrlich ascites test.

The results obtained are listed in the following table.

| Dose mg./kg. i.p. | Number of treatments | Frequency | Mean duration of life | | expressed in % of treated/ control |
|---|---|---|---|---|---|
| | | | expressed in days | | |
| | | | Treated | Control | |
| 3.2 | 9 | every day | 22.3 | 12.3 | 181 |
| 5.0 | 9 | every day | 21.5 | 13.2 | 163 |
| 6.4 | 9 | every day | 20.5 | 12.3 | 166 |
| 10 | 5 | every second day | 21.8 | 10.5 | 208 |
| 20 | 6 | every day | 8.5 | 13.2 | 64 |
| 20 | 1 | — | 19.4 | 10.5 | 185 |

From the table it can be seen that the duration of life of the tumorous animals has considerably been prolonged by administration of 3.2 to 6.4 mg/kg. doses every day. A 10 mg/kg. dose administered every second day had an even more favorable effect. It can also be seen that a single 20 mg/kg. dose is also effective, but this large dose cannot be administered every day due to its toxicity. A similar effect was achieved with 0.1 to 0.3 mg/kg/day doses of vincristine, 1.0 to 4.0 mg/kg/day doses of N-desmethyl-N-formyl-leurosine and 0.1 to 0.4 mg/kg/day doses of vinblastine.

EFFECT ON EHRLICH ASCITES CARCINOMA

Transplantation was carried out into outbred Swiss mice at a level of $5 \times 10^6$ ascites tumor cells. Administration of RGH-4451 was started 24 hours after transplantation. The results obtained are shown in the following table.

| Dose mg/kg i.p. | Number of treatments | Frequency | Mean duration of life | | expressed in % of treated/ Control |
|---|---|---|---|---|---|
| | | | expressed in days | | |
| | | | Treated | Control | |
| 1.0 | 9 | every day | 54.2 | 15.4 | 15.4 |
| 2.0 | 9 | every day | 43.0 | 16.4 | 261 |
| 4.0 | 9 | every day | 36.4 | 16.4 | 222 |
| 6.0 | 9 | every day | 48.2 | 15.9 | 303 |

| Dose mg./ Kg. i.p. | Number of treatments | Frequency | Mean duration of life | | expressed in % of treated*/ control | On the 65th day | |
|---|---|---|---|---|---|---|---|
| | | | expressed in days | | | alive | tumor-free |
| | | | treated | control | | | |
| 2.0 | 9 | every day | 64.1 | 16.4 | 392 | 9/10 | 6/10 |
| 4.0 | 9 | every day | 62.9 | 16.4 | 384 | 8/10 | 7/10 |
| 6.0 | 9 | every day | 65.8 | 16.7 | 394 | 8/10 | 4/10 |
| 20 | 1 | — | 65.5 | 16.7 | 392 | 8/10 | 3/10 |

*Keeping alive for four-times of the mean duration of life of the control group. The maximum is therefore 400%.

From the results it can be seen that the 2 to 6 mg./kg. doses administered once a day have a remarkable antitumor effect, a great part of the treated animals is tumor-free on the 65th day. A similar result is obtained when a single large dose is administered.

0.05 to 0.25 mg./kg. daily doses of vincristine and 1 to 4 mg./kg. daily doses of N-desmethyl-N-formyl-leurosine have a similar effect. In this case, however, the administration of a large single dose did not increase the duration of life.

EFFECT ON S 180 SC. CARCINOMA

S 180 sc. tumor tissues were transplanted into Swiss mice subcutaneously. Treatment was started 24 hours after transplantation. RGH-4451 was administered once a day in a dose of 2, 4, 8 and 16 mg./kg., respectively intraperitoneally. The tumor growth inhibition was evaluated on the 11th day on the basis of the weight of tumors. The change of the weight of spleen was also monitored.

The tumor growth inhibition observed upon administration of RGH-4451 was about the same as in the case of known diindole-alkaloids (34 to 56% depending on the dose) but the daily doses of the new compound could be higher and there was no substantial decrease in the weight of spleen even at as high doses as 16 mg./kg.

EFFECT OF GUERIN SC. CARCINOMA

Tumors were transplanted into Wistar rats subcutaneously. Administration of RGH-4451 was started on the day following the transplantation and the compound was administered six subsequent days intraperitoneally. The inhibition of tumor growth was evaluated on the 22nd day. The results obtained are listed in the following table.

| Dose mg./kg. i.p. | Weight of tumor | | Inhibition | Mortality until the 22nd day/number of animals |
|---|---|---|---|---|
| | Treated | Control | | |
| 2.0 | 10.7 | 18.9 | 43 | 0/6 |

| Dose mg./kg. i.p. | Weight of tumor | | | Mortality until the 22nd day/number of animals |
| --- | --- | --- | --- | --- |
| | Treated | Control | Inhibition | |
| 6.0 | 8.69 | 44.9 | 81 | 0/6 |
| 10.0 | 14.64 | 44.9 | 68 | 0/6 |
| 14.0 | — | — | — | 5/6 |

2 to 10 mg./kg. i.p. doses of RGH-4451 strongly inhibited the growth of Guerin carcinoma.

From the tests described hereinabove it can be concluded that 1.0 to 10.0 mg./kg. daily doses or 20 mg./kg. single doses of RGH-4451 have a significant tumor-growth inhibition effect and prolong the duration of life.

By contrast with vincristine, paralytic symptoms are entirely lacking even when sublethal doses are administered. The therapeutic effect of the tested new compound is greater than that of vincristine and N-desmethyl-N-formyl-leurosine as shown in the following table.

| | MTD/min eff. D |
| --- | --- |
| RGH-4451 | 10 |
| Vincristine | 6 |
| N-desmethyl-N-formyl-leurosine | 4 |

In the human therapy for infusion or intravenous administration 0.5 to 1.0 mg./kg. daily doses are advantageously used.

BRIEF DESCRIPTION OF THE DRAWING

FIG. 1 is an infrared spectrum of one of the compounds of present invention;

FIG. 2 is a nuclear magnetic resonance spectrum thereof;

FIG. 3 is another nuclear magnetic resonance spectrum thereof;

FIG. 4 is an infrared spectrum of another compound of the invention;

FIG. 5 is a nuclear magnetic resonance spectrum thereof; and

FIG. 6 is another nuclear magnetic resonance spectrum.

The invention relates to a process for the oxidation of vinblastine and leurosine or acid addition salts thereof by chromic acid or by an alkali metal dichromate in the presence of an organic solvent, glacial acetic acid and acetic anhydride at a low temperature, and optionally to the formylation of the mixture obtained. The process is characterized in carrying out the oxidation at a temperature of $-30°$ C. to $-90°$ C., preferably at a temperature not exceeding $-45°$ C. in a medium containing as an organic solvent a water-immiscible organic solvent, preferably a chlorinated hydrocarbon and optionally ethanol in a concentration lower than 10% relative to the volume of solvent, in the presence of glacial acetic acid and acetic anhydride, and adjusting the pH of the reaction mixture to 8 to 10, and (a) from the organic phase isolating the components of the product mixture obtained, i.e.

if vinblastine or an acid addition salt thereof is oxidized N-desmethyl-vinblastine, vincristine and optionally the compound designated "RGH-4451", which has the following characteristics:

melts at 235° C. to 238° C., has a specific rotatory power of $[\alpha]_D^{25} = +30.5°$ (c=1,chloroform), has an infrared spectrum as illustrated in FIG. 1, has a $^1$H-NMR spectrum illustrated in FIG. 2, has a $^{13}$C-NMR spectrum illustrated in FIG. 3, which render it highly probable that the structure of the molecule differs from vinblastine in containing an N—CH$_2$—O—C$_2$H$_5$ group in place of an N-methyl group, in the vindoline moiety of the molecule and has a molecular weight of 854.449 corresponding to the formula of $C_{48}H_{62}N_4O_{10}$; or if leurosine or an acid addition salt thereof is oxidized N-desmethyl-leurosine, N-desmethyl-N-formyl-leurosine and optionally new compound designated "RGH-4478" which has the following characteristics:

melts at 180° C. to 182° C., has a specific rotatory power of $[\alpha]_D^{25} = +59.25°$ (c=1, chloroform), has a infrared spectrum illustrated in FIG. 4, has a $^1$H-NMR spectrum illustrated in FIG. 5 and has a $^{13}$C-NMR spectrum illustrated on enclosure 6, which render it highly probable that the structure of this molecule differs from leurosine in containing an N—CH$_2$—O—C$_2$H$_5$ group in place of the N-methyl group in the vindoline moiety of the molecule, and has a molecular weight of 852 corresponding to the formula of $C_{48}H_{60}N_4O_{10}$ and, if desired, converting the products obtained into the acid addition salts thereof; or (b) optionally hydrolyzing the product mixture present in the organic phase, if desired formylating the mixture of N-desmethyl and N-desmethyl-N-formyl derivative obtained in a manner known per se, and isolating the N-desmethyl-N-formyl derivative obtained, i.e. vincristine if vinblastine or an acid-addition salt thereof is oxidized, or N-desmethyl-N-formyl-leurosine if leurosine or an acid addition salt thereof is oxidized, in a known manner, and if desired converting the product obtained into an acid addition salt thereof.

In the process according to the invention as a starting material technical or pharmacopeal vinblastine or a salt thereof, and leurosine or a salt thereof, respectively can be used. If an alkaloid of technical quality is employed, the product obtained can be purified for example, by chromatographic methods. If the starting material is of pharmacopeal quality, the product is directly suitable for therapeutical application. As an oxidizing agent chromic acid (CrO$_3$) or an alkali metal dichromate can be used.

Oxidation is carried out in the presence of acetic acid and acetic anhydride and of a water-immiscible organic solvent in which the alkaloids are readily soluble. Typical representatives of such solvents are benzene, chlorinated hydrocarbons, preferably chloroform or methylene chloride.

Optionally, i.e. if also "RGH"-compounds are to be prepared oxidation is carried out in the presence of ethanol. Ethanol is used in an amount of less than 10% related to the volume of the organic solvent, preferably in an amount of 0.1 to 3.0%.

The temperature of oxidation is between $-30°$ C. and $-90°$ C. N-desmethyl and N-desmethyl-N-formyl derivatives are always obtained under these conditions. If the reaction is carried out at a temperature not exceeding $-45°$ C. also "RGH"-compounds can be isolated. If the reaction is performed over $-45°$ C., only N-desmethyl and N-formyl derivatives are isolated.

When the oxidation is completed, the pH-value of the reaction mixture is adjusted to 8 to 10 taking care that the temperature does not exceed 50° C., and keeping the pH of the aqueous phase at or higher than 8.

The phases are then allowed to separate, and the alkaloids are isolated from the organic phase.

Following the reaction variant (a) the RGH-compound can also be isolated. In this case the alkaloid mixture obtained by evaporating the organic phase comprising the N-desmethyl derivative, N-desmethyl-N-formyl derivative and the "RGH"-compound is separated to its components by chromatography. Chromatography is performed on a column filled with partly deactivated alumina, carrying out the elution with various mixtures of benzene and a chlorinated hydrocarbon. The identification of the alkaloids present in the various fractions is effected by thin layer chromatography, the fractions containing the same alkaloids are combined and the alkaloids are isolated for example by evaporation. The alkaloids obtained, if desired, are purified and if desired are converted into pharmaceutically acceptable acid addition salts, preferably sulfate salts thereof.

If desired, the N-desmethyl derivative is formylated. As the formylating agent a mixture of formic acid and acetic anhydride is preferably used.

If the process variant (b) is followed, the RGH-compound is not isolated, instead, it can be converted into a corresponding N-desmethyl derivative by dilute aqueous acid, for instance a 0.5 to 5% aqueous sulphuric acid solution, hydrochloric acid solution or acetic acid.

The new compounds and/or acid-addition salts thereof can be transformed into pharmaceutical compositions, which are preferably administered parenterally.

The active ingredient is lyophilized, processed into dry ampoules, which are admixed with the contents of solvent ampoules containing the conventional additives, preferably immediately prior to administration.

In the solvent ampoules as a carrier preferably distilled water or a physiological sodium chloride solution is used, optionally together with a preserving agent (for example benzyl alcohol), antioxidant, milk sugar or buffers.

Administration is carried out in the form of infusion, preferably in a physiological saline solution.

The composition can contain also other pharmaceutically active compounds, for instance adjuvants (analgesics, cardiac restoratives), or other known cytostatics.

The present invention is further illustrated by the following non-limiting Examples.

EXAMPLE 1

5 g. (5.5 mmoles) of vinblastine sulfate are dissolved in a mixture of 1.2 lit. of a 1% solution of ethanol in chloroform and 250 ml. of acetic acid. The solution obtained is cooled to −55° C. and a solution of 2.48 g. (24.48 mmoles) of chromium trioxide in 930 ml. of acetic anhydride of −55° C. is added. The reaction mixture is stirred for 40 minutes, whereupon the pH is adjusted to 9 to 10 with a concentrated aqueous ammonium hydroxide solution having a temperature of −45° C. to −50° C. Thereafter 5 lit. of water are added to the two-phase reaction mixture and after a five-minute stirring the phases are allowed to separate. The chloroform phase is put aside and the aqueous phase is extracted with 0.5 lit. of chloroform. The chloroform phases are combined and treated with two 2.5 lit.-portions of a 1% aqueous ammonium hydroxide solution. The phases are reseparated, and the chloroform phase is dried over sodium sulphate, filtered and the filtrate is evaporated to dryness under reduced pressure.

4.0 g. of a mixture of vinblastine derivatives are obtained, which can be separated to the corresponding components by following the method described hereinbelow:

The product obtained (4.0 g.) is dissolved in 24 ml. of a 2:1 mixture of benzene and chloroform. The solution is then passed through a chromatographic column filled with 200 g. of alumina having an activity grade of III, which has previously been wetted with a 2:1 mixture of benzene and chloroform. The alkaloids are eluted by using the following eluants in the given order:

1.2 lit. of a 2:1 mixture of benzene and chloroform,
1.5 lit. of a 1:1 mixture of benzene and chloroform,
0.9 lit. of a 1:2 mixture of benzene and chloroform.

The various fractions obtained are examined by thin layer chromatography (t.l.c.).

(a) Processing of the fraction obtained by elution with a 2:1 mixture of benzene and chloroform The first 400-ml. fraction of the eluate is alkaloidfree, the further eluates obtained with a 2:1 mixture of benzene and chloroform contain a new compound. By combining and evaporating the alkaloid-containing fractions 1.88 g. of a crude new compound are obtained. The compound is designated as "RGH-4451".

One or more recrystallizations of the crude product from a double amount of ethanol yields 1.30 g. of a crystalline, chromatographically uniform RGH-4451 product, having a melting point of 235° C. to 238° C. (decomp., after recrystallization from ethanol twice). $[\alpha]_D^{25} = +30.5°$ (c=1, chloroform)

$R_f$=0.62 (adsorbent: silica gel; eluting mixture: 100:5:5:5 mixture of diethyl ether, ethanol, benzene and diethyl amine).

Mass spectrum: According to the mass spectrum the molecular weight of the compound amounts to 854.449, which corresponds to the formula of $C_{48}H_{62}N_4O_{10}$. The mass number of this molecule is greater than that of vinblastine with 44, which corresponds to a $C_2H_4O$ unit. On the basis of fragmentation studies it could be unambiguously concluded that said unit is linked to the vindoline part of the molecule.

The $^1$H-NMR spectrum is shown on FIG. 2. From this spectrum the N-methyl singulette present at 2.73 ppm in the spectrum of vinblastine is lacking. On the other hand at 4.48 ppm the multiplette peak of the methylene of the group N—$CH_2$—O can be seen, while the methyl triplette and methylene quartette of the group O—$C_2H_5$ appear at 1.05 and 3.35 ppm., respectively.

The $^{13}$C—NMR spectrum is shown on FIG. 3. The presence of the group N—$CH_2$—O is verified by the peak at 64.42 ppm. (which has a triplette multiplicity in the off-resonancy spectrum).

On the basis of the above analysis, a —$CH_2$—O—$C_2H_5$ group is present in the molecule.

The IR spectrum of the compound can be seen on the FIG. 1, where the characteristic group frequencies are as follows:

| | |
|---|---|
| 3470 cm$^{-1}$ | OH valence |
| 2970–2830 cm$^{-1}$ | OH valence vibrations |
| 1737 and 1230 cm$^{-1}$ | acetyl groups |
| 1612 cm$^{-1}$ | C=C bond |
| 1595 cm$^{-1}$ | aromatic skeleton |
| 742 cm$^{-1}$ | 4 AK-H next to each other. |

The characteristic new bands of RGH-4451 having a low intensity appear at 995, 1170 and 1360 cm$^{-1}$.

It can also be seen that the low-frequency bands at 1090 cm$^{-1}$ and 700 cm$^{-1}$ characteristic of vinblastine disappear.

(b) Processing of the fraction obtained by elution with 1:1 mixture of benzene and chloroform The first 1000–1200 ml. fraction of the eluate obtained when eluting with 1.5 lit. of a 1:1 mixture of benzene and chloroform is a so called mixed fraction consisting of the new compound called RGH-4451 and N-desmethyl-vinblastine, while the remaining 300 to 500 ml.-fraction contains N-desmethyl-vinblastine.

The mixed fraction is evaporated to give 0.57 g. of a mixed solid, which is converted into N-desmethyl-vinblastine by the following technique: The evaporation residue is dissolved in 10 ml. of benzene, the benzene solution is extracted with three 15-ml. portions of a 2% aqueous hydrochloric acid solution, the phases are separated, whereupon the pH of the aqueous phase is adjusted to 9 with a concentrated aqueous ammonium hydroxide solution. The obtained alkaline solution is extracted with three 10-ml. portions of chloroform, and the chloroform extract is evaporated. 0.56 g. of N-desmethyl-vinblastine are obtained.

By evaporating the N-desmethyl-vinblastine fractions 0.08 g of N-desmethyl-vinblastine are obtained, which is combined with N-desmethyl-vinblastine obtained from the mixed fraction. N-desmethyl-vinblastine is converted into vincristine as described in the Hungarian Patent Specification No. 165,599.

Yield: 0.63 g. of vincristine.
Melting point: 218°1 C. to 220° C.

(c) Processing of the fraction obtained by elution with a 1:2 mixture of benzene and chloroform From the fraction obtained by elution with 0.9 lit. of a 1:2 mixture of benzene and chloroform vincristine can be isolated by evaporation.

Yield: 1.22 g. of vincristine
Melting point: 220° C.

EXAMPLE 2

5 g. (5.5 mmoles) of vinblastine sulfate are dissolved in a mixture of 1.2 lit. of a 1% solution of ethanol in chloroform and 250 ml. of acetic acid. The solution obtained is cooled to −55° C. and a solution of 2.48 g. (24.48 mmoles) of chromium trioxide in 930 ml. of acetic anhydride of −55° C. is added. The reaction mixture is stirred for 40 minutes, whereupon the pH is adjusted to 9 to 10 with a concentrated aqueous ammonium hydroxide solution cooled to −45° C. to −50° C. Thereafter 5 lit. of water are added to the two-phase reaction mixture and after a five-minute stirring the phases are allowed to separate. The chloroform phase is put aside and the aqueous phase is extracted with 0.5 lit. of chloroform. The chloroform phases are combined and treated with two 2.5-lit. portions of a 1% aqueous ammonium hydroxide solution. The phases are reseparated, and the chloroform phase is extracted with three 0.3-lit. portions of an aqueous sulfuric acid solution, whereupon the pH of the extract is adjusted to 9 with a concentrated aqueous ammonium hydroxide solution. The alkaline extract is extracted with three 0.2-lit. portions of chloroform. Evaporation of the extract affords an evaporation residue consisting of N-desmethyl-vinblastine and vincristine, which is converted to vincristine by formylation carried out as described in Hungarian Patent Specification No. 165,599. Treating with a solution of sulfuric acid in ethanol, the product obtained can be converted into vincristine sulfate.

Yield: 3.6 g. of vincristine sulfate.

EXAMPLE 3

5 g. (5.5 mmoles) of vinblastine sulfate are dissolved in a mixture of 1.2 lit. of a 1% solution of ethanol in chloroform and 250 ml. of acetic acid. The solution obtained is cooled to −55° C. and a solution of 2.48 g. (24.48 mmoles) of chromium trioxide in 930 ml. of acetic anhydride of −55° C. is added. The reaction mixture is stirred for 40 minutes, whereupon it is poured into a mixture of 6 lit. of water and 4 lit. of a concentrated aqueous ammonium hydroxide solution cooled to +2° C. to +5° C. The reaction mixture is stirred for 5 minutes at a temperature below 20° C., ensuring that the pH-value of the aqueous phase remains at least 8. The phases are then separated, the aqueous phase is extracted with 0.5 lit. of chloroform and the extract is combined with the chloroform phase. The chloroform solution is extracted with two 2.5-lit. portions of a 1% aqueous ammonium hydroxide solution, the phases are separated and the chloroform phase is dried. It is then (a) either evaporated according to Example 1, followed by separating the diindole-alkaloid mixture obtained weighing 4 g. into its components, or (b) is converted into vincristine by an acid treatment and a subsequent formylation as described in Example 2.

If the (a) reaction route is followed the yield is identical with that obtained in Example 1, while the (b) reaction route affords the same yield as Example 2.

EXAMPLE 4

5 g. (5.5 mmoles) of vinblastine sulfate are dissolved in a mixture of 1.2 lit. of a 0.5% solution of ethanol in methylene chloride and 250 ml. of acetic acid. The solution obtained is cooled to −55° C. and a solution of 2.48 g. (24.48 mmoles) of chromium trioxide in 930 ml. of acetic anhydride of −55° C. is added. The reaction mixture is stirred for 40 minutes, whereupon the pH is adjusted to 9 to 10 with a concentrated aqueous ammonium hydroxide solution cooled to −45° C. to −50° C. Thereafter 5 lit. of water are added to the two-phase reaction mixture and after a five-minute stirring the phases are allowed to separate. The methylene chloride phase is put aside and the aqueous phase is extracted with 0.5 lit. of methylene chloride. The methylene chloride phases are combined and treated with two 2.5-lit. portions of a 1% aqueous ammonium hydroxide solution. The phases are reseparated, the methylene chloride phase is dried with sodium sulfate, filtered, whereupon the filtrate is evaporated to dryness under reduced pressure.

Yield: 3.5 g. of a mixture of diindole-alkaloids, which is separated into its components following the method described in Example 1.

The physical characteristics of RGH-4451 and vincristine, respectively are identical with the corresponding characteristics of the products of Example 1.

EXAMPLE 5

5 g. of leurosine sulfate are dissolved in a mixture of 1.2 lit. of a 1% solution of ethanol in chloroform and 250 ml. of acetic acid. The solution obtained is cooled to −55° C. and a solution of 2.48 g. (24.48 mmoles) of chromium trioxide in 930 ml. of acetic anhydride of −55° C. is added. The reaction mixture is stirred for 40 minutes, whereupon the pH is adjusted to 9 to 10 with a concentrated aqueous ammonium hydroxide solution having a temperature of −45° C. to −50° C. Thereafter 5 lit. of water are added to the two-phase reaction mixture and after a five-minute stirring the phases are allowed to separate. The chloroform phase is put aside and the aqueous phase is extracted with 0.5 lit. of chloroform. The chloroform phases are combined and extracted with two 2.5-lit. portions of a 1% aqueous ammonium hydroxide solution. The phases are reseparated, the chloroform phase is dried with sodium sulfate, filtered, whereupon the filtrate is evaporated to dryness under reduced pressure.

Yield: 4.5 g. of a mixture of leurozine derivatives, which is separated to the corresponding components by following the method described hereinbelow:

The product obtained (4.5 g.) is dissolved in 27 ml. of a 3:1 mixture of benzene and chloroform, and the solution is chromatographed on a column filled with alumina having an activity grade of III and treated with a 3:1 mixture of benzene and chloroform. The alkaloids are eluted with the following eluants in the given order:

3.5 lit. of a 3:1 mixture of benzene and chloroform,
1 lit. of a 2:1 mixture of benzene and chloroform,
2.5 lit. of a 1:2 mixture of benzene and chloroform.

250-ml. fractions are collected and the alkaloids contained therein are examined by thin layer chromatography (t.l.c.).

The 1st to 6th fractions (1.5 lit.) are alkaloid-free, the 7th to 14th fractions (3:1 mixture of benzene and chloroform) and the 15th to 17th fractions (2:1 mixture of benzene and chloroform) contain the new compound indentified RGH-4478. The 18th fraction obtained with a 2:1 mixture of benzene and chloroform and the 19th to 23rd fractions obtained with a 1:2 mixture of benzene and chloroform contain N-desmethyl-leurosine, while the 24th to 28th fractions obtained by elution with a 1:2 mixture of benzene and chloroform contain N-desmethyl-N-formyl-leurosine.

The eluate fractions are processed as follows:

(a) The 7th to 17th fractions are combined and evaporated. 2.13 g. of crude RGH-4478 are obtained, which is purified by crystallization from 5 ml. of ethanol at 5° C. If desired, the product is dissolved in chloroform, the solution obtained is evaporated, whereupon crystallization from ethanol is repeated.

Yield: 1.6 g. of RGH-4478

Melting point: (after recrystallization from ethanol twice): 180° C. to 182° C.

$[\alpha]_D^{25} = +59.25°$ (c=1, chloroform).

$R_f = 0.37$ (adsorbent: silica gel; eluting mixture: a 100:5:5:5 mixture of diethyl ether, ethanol, benzene and diethyl amine).

Molecular weight: 852.

The $^1$H-NMR spectrum is shown in FIG. 5. From this spectrum the N-methyl singulette characteristic of starting material is lacking. On the other hand at 4.48 ppm. the multiplette peak of the methylene of the group —N—CH$_2$—O can be seen, while the methyl triplette and methylene quartette of the group O—C$_2$H$_5$ appear at 1.10 and 3.38 ppm., respectively.

The $^{13}$C-NMR spectrum is shown in FIG. 6, while the IR spectrum is attached as FIG. 4.

The characteristic group frequencies of the IR spectrum of the product are as follows:

| | |
|---|---|
| 3470 cm$^{-1}$ | OH valence |
| 2970–2830 cm$^{-1}$ | OH valence vibrations |
| 1737 and 1230 cm$^{-1}$ | acetyl groups |
| 1612 cm$^{-1}$ | C=C bond |
| 1595 cm$^{-1}$ | aromatic skeleton |
| 742 cm$^{-1}$ | 4 AK-H next to each other |
| 823 cm$^{-1}$ | epoxide ring |

(b) The 18th to 23rd fractions are combined. The RGH-4478 traces are eliminated by extraction with a 2% sulfuric acid solution, and adjustment of the pH of the acid aqueous phase to 9 with a concentrated aqueous ammonium hydroxide solution. The solution is then extracted with three 0.2-lit. portions of chloroform and the chloroform extract is evaporated.

Yield: 0.25 g. of N-desmethyl-leurosine.

The product obtained, if desired, is converted into N-desmethyl-N-formyl-leurosine by formylation carried out as described in the Hungarian Patent Specification No. 165,986.

Yield: 0.24 g. of N-desmethyl-N-formyl-leurosine (c) The 24th to 28th fractions are combined and evaporated.

Yield: 4.42 g. of N-desmethyl-N-formyl-leurosine.

EXAMPLE 6

Following the procedure described in Example 2 but starting from 5 g. of leurosine sulfate instead of vinblastine sulfate 3.7 g. of N-desmethyl-N-formyl-leurosine sulfate are obtained.

EXAMPLE 7

5 g. (5.5 mmoles) of vinblastine sulfate dried until alcohol-free are dissolved in 1000 ml. of ethanol-free methylene chloride, and to the solution 120 ml. of acetic acid and 3.2 ml. (10 equivalent) of ethanol are added. The solution is cooled to −55° C. and a solution of 2.5 g. of chromium trioxide in 470 ml. of acetic anhydride cooled to −55° C. is added. The reaction mixture is stirred at −55° C. for 40 to 45 minutes, whereupon the pH is adjusted and the methylene chloride phases are evaporated as described in Example 4.

Yield: 4 g. of a diindole-alkaloid mixture.

The 4 g. mixed product obtained is dissolved in a 8:2 mixture of benzene and chloroform and the solution is passed through a chromatographic column filled with 200 g. of alumina, having an activity grade of III. Elution is carried out in the following way:

As an eluent initially 5 to 6 lit. of a 8:2 mixture of benzene and chloroform are used, the eluates are combined and evaporated. 2.4 g. of crude RGH-4451 are obtained. Recrystallization of the crude product from ethanol affords crystalline RGH-4451, which has the same characteristics as described in Example 1.

Elution is then repeated with 3 to 4 lit. of a 1:1 mixture of benzene and chloroform. The combined fractions containing N-desmethyl-vinblastine as well as the fractions containing vincristine are combined and evaporated separately.

Yield: 0.4 g. of N-desmethyl-vinblastine and 0.8 g. of vincristine.

EXAMPLE 8

Following the procedure described in Example 7 but carrying out the reaction in the presence of 9.5 ml. (30 equivalent) of ethanol, the products of Example 7 are obtained, with the same yields. The physical characteristics of the products are also identical with those described in Example 7.

What we claim is:

1. A compound RGH-4451 or a pharmaceutically acceptable acid addition salt thereof wherein the compound RGH-4451 has the following characteristics:
melts at 235° C. to 238° C.,
has a specific rotary power of $[\alpha]_D^{25} = +30.5°$, (c=1, chloroform),
has an infrared spectrum illustrated in FIG. 1,
has a $^1$H-NMR spectrum illustrated in FIG. 2,
has a $^{13}$C-NMR spectrum illustrated in FIG. 3, and
has a molecular weight of 854.449
indicating that RGH-4451 differs from vinblastine in containing a N—CH$_2$—O—C$_2$H$_5$ group in place of an N-methyl group in the vindoline moiety of the molecule.

* * * * *